US009877918B2

(12) United States Patent
Yamashita et al.

(10) Patent No.: US 9,877,918 B2
(45) Date of Patent: *Jan. 30, 2018

(54) LONG-LASTING CONTROLLED-RELEASE LIPOSOME COMPOSITION AND METHOD FOR PRODUCING SAME

(71) Applicant: TERUMO KABUSHIKI KAISHA, Tokyo (JP)

(72) Inventors: Keiko Yamashita, Ashigarakami-gun (JP); Shigenori Nozawa, Ashigarakami-gun (JP); Naoki Otomo, Ashigarakami-gun (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 380 days.

This patent is subject to a terminal disclaimer.

(21) Appl. No.: 13/947,581

(22) Filed: Jul. 22, 2013

(65) Prior Publication Data

US 2013/0309297 A1    Nov. 21, 2013

Related U.S. Application Data (63) Continuation of application No. PCT/JP2012/057376, filed on Mar. 22, 2012.

(30) Foreign Application Priority Data

Mar. 25, 2011 (JP) ................................. 2011-068052

(51) Int. Cl.
| | |
|---|---|
| A61K 9/127 | (2006.01) |
| A61K 31/27 | (2006.01) |
| A61K 31/407 | (2006.01) |
| A61K 31/445 | (2006.01) |
| A61K 31/519 | (2006.01) |
| A61K 31/55 | (2006.01) |

(52) U.S. Cl.
CPC ............ *A61K 9/1277* (2013.01); *A61K 9/127* (2013.01); *A61K 9/1278* (2013.01); *A61K 31/27* (2013.01); *A61K 31/407* (2013.01); *A61K 31/445* (2013.01); *A61K 31/519* (2013.01); *A61K 31/55* (2013.01)

(58) Field of Classification Search
CPC .... A61K 9/127; A61K 9/1271; A61K 9/1278; A61K 47/28; A61K 51/1234; A61K 51/0408
See application file for complete search history.

(56) References Cited

U.S. PATENT DOCUMENTS

| | | | |
|---|---|---|---|
| 4,687,661 A | 8/1987 | Kikuchi et al. | |
| 5,192,549 A | 3/1993 | Barenolz et al. | |
| 6,162,462 A * | 12/2000 | Bolotin ................ | A61K 31/445 264/4.1 |
| 2004/0142025 A1 | 7/2004 | MacLachlan et al. | |
| 2008/0031935 A1 * | 2/2008 | Bodenteich ............ | A61K 9/127 424/450 |
| 2009/0041833 A1 | 2/2009 | Bettinger et al. | |
| 2010/0021531 A1 | 1/2010 | Yoshino et al. | |
| 2011/0183954 A1 | 7/2011 | Almeida et al. | |

FOREIGN PATENT DOCUMENTS

| | | |
|---|---|---|
| EP | 2656835 A1 | 10/2013 |
| JP | 60-7932 A | 1/1985 |
| JP | 6-239734 A | 8/1994 |
| JP | 2659136 B2 | 9/1997 |
| JP | 2847065 B2 | 1/1999 |
| JP | 2005-538967 A | 12/2005 |
| JP | 2008-106001 A | 5/2008 |
| JP | 2008-538367 A | 10/2008 |
| JP | 2009-132629 A | 6/2009 |
| JP | 2011-522870 A | 8/2011 |
| WO | WO 1986/001102 A1 | 2/1986 |
| WO | 2004/002453 A1 | 1/2004 |
| WO | 2007/049278 A2 | 5/2007 |

(Continued)

OTHER PUBLICATIONS

Vemuri, S. and Rhodes, C. T. (1994). "Development and Characterization of a Liposome Preparation by a pH-Gradient Method." J. Pharm. Pharmacol., 46: 778-783.*

Haran et al., "Transmembrane Ammonium Sulfate Gradients in Liposomes Produce Efficient and Stable Entrapment of Amphipathic Weak Bases", Biochimica et Biophysica Acta (BBA), (Sep. 19, 1993), vol. 1151, No. 2, pp. 201-215, XP023352276.

The extended European Search Report dated Sep. 11, 2004, by the European Patent Office in corresponding European Patent Application No. 12763544.9-1455. (9 pages).

(Continued)

*Primary Examiner* — Tracy Lu (74) *Attorney, Agent, or Firm* — Buchanan, Ingersoll & Rooney PC (57) ABSTRACT

A liposome composition, which is obtained by mixing a water-miscible organic solution in which a phospholipid and cholesterol are contained in a total concentration of 100 to 200 w/v % in a water-miscible organic solvent with a first aqueous phase solution in an amount of 3/1 to 12/1 in terms of volume ratio to the water-miscible organic solution, thereby obtaining an emulsion in which the total concentration of the phospholipid and cholesterol in the resulting mixed phase is 15 to 50 w/v %, followed by subjecting the emulsion to external solution exchange with a second aqueous phase solution, wherein an ion gradient is formed between an aqueous phase in an internal region of a liposome membrane, including the first aqueous phase solution, and an aqueous phase in an external region of the liposome membrane, including the second aqueous phase solution, and a drug can be introduced in a high encapsulation amount.

18 Claims, 3 Drawing Sheets

(56) References Cited

FOREIGN PATENT DOCUMENTS

WO     WO 2007049278 A2 *   5/2007   ............. A61K 9/127
WO     WO 2009/150462 A1    12/2009

OTHER PUBLICATIONS

Office Action dated Nov. 12, 2014, issued by the Russian Patent Office in corresponding Russian Patent Application No. 2013147619 and an English translation of the Office Action. (12 pages).

E. Davisson et al., "High-Dose Bupivacaine Remotely Loaded into Multivesicular Liposomes Demonstrates Slow Drug Release Without Systemic Toxic Plasma Concentrations After Subcutaneous Administration in Humans", Anesthetic Pharmocology and Prectinical Pharmacology, Apr. 2010, pp. 1018-1023, vol. 110, No. 4.

G. Grant et al., "A Novel Liposomal Bupivacaine Formulation to Produce Ultralong-Acting Analgesia", Anesthesiology, Jul. 2004, pp. 133-137, vol. 101, No. 1.

International Search Report (PCT/ISA/210) dated Apr. 24, 2012, by the Japanese Patent Office as the International Searching Authority for International Application No. PCT/JP2012/057376 with translation (4 pages total).

* cited by examiner

LONG-LASTING CONTROLLED-RELEASE LIPOSOME COMPOSITION AND METHOD FOR PRODUCING SAME

RELATED APPLICATIONS

This application claims priority as a continuation application under 35 U.S.C. § 120 to International Application No. PCT/JP2012/057376 filed on Mar. 22, 2012, designating the U.S., and which claims priority to Japanese Application No. 2011-068052 filed on Mar. 25, 2011, the entire content of both of which is incorporated herein by reference.

TECHNICAL FIELD

Disclosed is a long-lasting controlled-release liposome composition which contains an effective component such as a drug.

BACKGROUND DISCUSSION

In recent years, as a consequence of an aging society, there has been an increase in the number of patients who need a care giver, such as patients who suffer from dementia, brain diseases, Parkinson's disease and the like. Such patients may forget to take medicine or may experience difficulty in taking medicine because of difficulty in swallowing. Thus, it is difficult for these patients to manage the medicine-taking activity by themselves. Therefore, there is a demand for other administering method than peroral administration. Besides, in the cases of patients who are treated with anti-mental illness drugs, their living is hindered due to appearance of symptoms as soon as the drug stops working. In such cases, therefore, administration should be repeated several times per day, before the drug's efficacy is lost. Frequent administration imposes a heavy burden on the patient. Accordingly, long-lasting controlled-release preparations are highly desired in all disease regions.

Most of the controlled-release preparations which have been investigated heretofore as preparations for subcutaneous administration or intramuscular administration are microspheres based on polylactic acid-glycolic acid copolymer (PLGA). For instance, there is a microcapsule preparation Leuplin (registered trademark) in which leuprorelin as a carcinostatic agent is encapsulated in a cross-linked matrix of PLGA. These microspheres based on PLGA are known to release the drug immediately upon administration (initial burst), and the concentration of the agent in the blood is immediately raised to above the effective concentration. This leads to the possibility of side effects. Besides, in the case of using PLGA, it is difficult to encapsulate a drug in a high concentration and with a high efficiency. On a clinical basis, on the other hand, there is a limit as to the dose in which the drug can be administered. Therefore, there are problems yet to be solved in relation to an improvement in the amount of drug encapsulation. Further, in the case of using PLGA, an organic solvent is used in the preparation process, so that the removal of the organic solvent from the preparation is indispensable. This is often difficult to achieve in the manufacture on an industrial scale. In addition, PLGA is said to have a serious problem in that local intensification of acid attendant on the hydrolysis can cause inflammation in the administration region.

Other than the above, some approaches have been made in which bupivacaine is encapsulated in multilayer membrane liposomes by the remote loading method. In various documents, however, the relationship between particle diameter and controlled-release properties has not been disclosed, and no finding has been obtained as to the optimum particle diameter in the controlled-release preparations. In addition, the controlled-release times disclosed in the documents cannot be said to be sufficient on a clinical basis, see (Anesthesiology 101 (2004) 133-137, International Society for Anaesthetic Pharmacology 110 (2004) 1018-1023). Furthermore, the multivesicular liposome (MVL) described in JP-T-2001-522870 has been developed as a lipid-based controlled-release drug support for local or systemic drug delivery. This approach, however, is also not yet satisfactory and still has problems to be solved, with respect to the drug encapsulation amount and the controlled-release time.

SUMMARY

According to one aspect, disclosed is a liposome composition obtained by mixing a water-miscible organic solution in which a phospholipid and cholesterol are contained in a total concentration of 100 to 200 w/v % in a water-miscible organic solvent with a first aqueous phase solution in an amount of 3/1 to 12/1 in terms of volume ratio to the water-miscible organic solution, thereby obtaining an emulsion in which the total concentration of the phospholipid and cholesterol in the resulting mixed phase is 15 to 50 w/v %, followed by subjecting the emulsion to external solution exchange with a second aqueous phase solution, wherein an ion gradient is formed between an aqueous phase in an internal region of a liposome membrane, the internal-region aqueous phase including the first aqueous phase solution, and an aqueous phase in an external region of the liposome membrane, the external-region aqueous phase including the second aqueous phase solution.

BRIEF DESCRIPTION OF DRAWINGS

FIG. 1 shows electron microscopic observation photographs of a freeze-fractured replica of a donepezil liposome preparation obtained in Preparation Example 2, wherein FIG. 1a is a fracture view taken near the outermost surface of the liposome preparation, and FIG. 1b is a fracture view taken substantially at the center of the liposome preparation.

DETAILED DESCRIPTION

According to an illustrative aspect, disclosed is a liposome composition making it possible to obtain a liposome preparation having long-lasting controlled-release properties by which a drug can be administered in a clinically required quantity and in a small volume and, further, a clinically effective drug concentration in blood can be stably maintained for a long period of time.

It has been determined that when a drug is encapsulated in a liposome composition which includes a uniform internal aqueous phase in a multilayer membrane having a structure of 12 or more layers in which an ion gradient is formed between an internal aqueous phase and an external aqueous phase of liposomes (hereinafter sometimes referred to as empty liposomes), a liposome preparation having long-lasting controlled-release properties can be obtained.

Disclosed are the following illustrative aspects.

(1) A liposome composition obtained by mixing a water-miscible organic solution in which a phospholipid and cholesterol are contained in a total concentration of 100 to 200 w/v % in a water-miscible organic solvent with a first aqueous phase solution in an amount of 3/1 to 12/1 in terms of volume ratio to the water-miscible organic solution, thereby obtaining an emulsion in which the total concentration of the phospholipid and cholesterol in the resulting mixed phase is 15 to 50 w/v %, followed by subjecting the emulsion to external solution exchange with a second aqueous phase solution, wherein an ion gradient is formed between an aqueous phase in an internal region of a liposome membrane, the internal-region aqueous phase including the first aqueous phase solution, and an aqueous phase in an external region of the liposome membrane, the external-region aqueous phase including the second aqueous phase solution.

(2) The liposome composition as described in the above paragraph (1), wherein the ion gradient is a pH proton gradient, and the liposome composition has the pH gradient such that the pH of the aqueous phase in the internal region of a liposome (hereinafter sometimes referred to as internal aqueous phase) is lower than the pH of the aqueous phase in the external region of the liposome (hereinafter sometimes referred to as external aqueous phase).

(3) The liposome composition as described in the above paragraph (1) or (2), wherein the liposome has the internal-region aqueous phase inside a multilayer membrane having an average particle diameter in terms of outermost diameter of equal to or greater than 2.5 μm and having a structure of 12 or more layers.

(4) A liposome preparation including a drug introduced into the aqueous phase in the internal region in the liposome composition as described in any of the above paragraphs (1) to (3) by use of the ion gradient, wherein the drug is present in the liposome in a molar ratio of 0.08 (mol) or more based on the total lipid (mol).

(5) The liposome preparation as described in the above paragraph (4), wherein the liposome preparation has either systemic controlled-release properties, such that an in-blood effective concentration of the drug encapsulated in the internal region is maintained for equal to or more than four days, or local controlled-release properties, such that a local effective concentration of the drug encapsulated in the internal region is maintained for equal to or more than four days.

(6) The liposome preparation as described in the above paragraph (4) or (5), wherein the drug is an amphipathic weakly basic compound.

(7) A long-lasting controlled-release preparation kit including the liposome preparation as described in any of the above paragraphs (4) to (6) and an injection needle having at least one gauge size selected from among 27 to 33 gauge.

In a further illustrative embodiment, the liposome composition may contain a liposome other than the liposome of the previously described liposome composition. Examples of the other liposome than the liposome of the liposome composition include single lamella small liposomes and multivesicular liposomes. The liposome of the previously described liposome composition can account for 50 mass % or more, for example 60 mass % or more, for example 80 mass % or more, of the total mass of liposomes present in the composition.

The liposome composition permits a drug to be encapsulated therein highly efficiently when lipids are present in a specified total lipid concentration, whereby a liposome preparation with a high drug concentration can be obtained. In addition, the liposome composition wherein the internal-region aqueous phase is present inside a multilayer membrane ensures that when a drug is encapsulated in the liposome composition to obtain a liposome preparation, the drug can be stably released in a sustained manner for a long period of time while keeping a clinically effective drug concentration in the blood and without any initial burst. The liposome preparation can reduce the fear of side effects, and the number of times of administration can also be reduced. Therefore, the liposome preparation is very useful. Furthermore, the liposome preparation can administer the required quantity of a drug in a small volume. Generally, preparations for subcutaneous or intramuscular administration are administered using a thick needle of 19 to 21 gauge. On the other hand, the described liposome preparation can be administered even by small-diameter needles of high gauge numbers. Thus, the described liposome preparation can markedly enhance a patient's quality of life.

In an illustrative embodiment, a liposome is provided that includes a plurality of lipid bilayers having a specified particle diameter (outermost diameter of liposome particles) and has one internal aqueous phase therein. The average particle diameter of the illustrative liposomes can be 2.5 to 12 μm. For example, the average particle diameter is 3.7 to 10 μm, for example 5 to 10 μm, for example 6 to 10 μm. The liposomes can have an average particle diameter of 2.5 μm or more. The particle diameter of the liposomes can be measured as an average particle diameter (average outermost diameter) by use of a particle size distribution meter (for instance, a light scattering diffraction particle size distribution analyzer, e.g., Beckman Coulter LS230).

In an illustrative embodiment, the liposome has a wall composed of lipid bilayers. Assuming that one layered structure (lamellarity) is composed of one lipid bilayer, the liposome has a configuration wherein an outer shell as a wall is composed of a specified number of layered structures. Especially, the liposome has a layered structure of 12 to 35 layers (12-ply to 35-ply) (the (average particle diameter) of the liposome when having the layered structure being 2.5 to 12 μm). For example, the liposome has a layered structure of 14 to 27 layers (14-ply to 27-ply) (the outside diameter (average particle diameter) of the liposome when having the layered structure being 3.7 to 10 μm). These layered structures are so arranged that the layered structures adjacent to each other in an inside-outside relationship are present substantially in contact with each other, with a tiny amount of water present therebetween. The number of the layered structures can be determined by taking a scanning electron microscope (SEM) photograph under such a condition as to break part of the wall of the liposome and counting the number of the layered structures.

The liposome has an internal aqueous phase in the inside thereof. The internal aqueous phase is configured in an inside region of an inside surface of the layered structure present on the most inner side. The thickness of one layered structure (lipid bilayer) is about 10 nm, and the wall thickness of the liposome is generated according to the number of the lipid bilayers which are present. Where the layered structure of the lipid bilayers has 20 layers, 20 layers with 10 nm thickness are arranged on both sides of the internal aqueous phase, so that the thickness of both walls is 0.4 µm. By subtracting 0.4 µm from the outside diameter of the liposome composed of 20 layers, the inside diameter of the internal aqueous phase can be calculated. The inside diameter of the internal aqueous phase of the liposome composition and preparation is, for example, 2.2 µm (12 layers with an average particle diameter of 2.5 µm) to 11.3 µm (35 layers with an average particle diameter of 12 µm) and can be 3.4 µm (14 layers with an average particle diameter of 3.7 µm) to 9.4 µm (27 layers with an average particle diameter of 10 µm). The liposome in the liposome preparation has, for example, a layered structure of 12 layers when the average particle diameter is 2.5 µm. Similarly, the liposome has, for example, a layered structure of 14 layers when the average particle diameter is 3.7 µm. For example, the layered structure has 27 layers when the average particle diameter is 10 µm, and the layered structure has 35 layers when the average particle diameter is 12 µm.

The liposome produced in such a manner ensures that favorable controlled-release properties can be obtained, and a uniform liposome composition can be produced.

The liposome can be obtained by the following steps, and forms the previously described liposome composition by being dispersed in an aqueous phase in an external region.

The liposome is "a liposome obtained by mixing a water-miscible organic solution in which a phospholipid and cholesterol are contained in a total concentration (hereinafter sometimes referred to as total lipid concentration) of 100 to 200 w/v % (100 to 200 g in 100 ml) in a water-miscible organic solvent with a first aqueous phase solution in an amount of 3/1 to 12/1 in terms of volume ratio to the water-miscible organic solution, thereby obtaining an emulsion in which the total concentration of the phospholipid and cholesterol in the resulting mixed phase is 15 to 50 w/v % (15 to 50 g in 100 ml), followed by subjecting the emulsion to external solution exchange with a second aqueous phase solution."

As used herein, the "water-miscible organic solvent" is any of alcohols such as methanol, ethanol, isopropyl alcohol, and butanol, among which preferred is ethanol.

As used herein, the "water-miscible organic solution (hereinafter sometimes referred to as alcohol solution)" is a solution in which a phospholipid and cholesterol are contained in an alcohol in a total concentration of 100 to 200 w/v % (100 to 200 g in 100 ml).

As used herein, the "mixed phase" is a mixed phase which is obtained by mixing the water-miscible organic solution with the first aqueous phase solution in an amount of 3/1 to 12/1 in terms of volume ratio to the water-miscible organic solution, and which has a total lipid concentration of 15 to 50 w/v % (15 to 50 g in 100 ml).

As used herein, the "first aqueous phase," also called the aqueous phase in an internal region or the internal aqueous phase, is the aqueous phase in the internal region present uniformly inside a multilayer membrane of the liposome.

As used herein, the "second aqueous phase," also called the aqueous phase in an external region or the external aqueous phase, is an aqueous phase which is present in the exterior of the multilayer membrane of the liposome, and which forms an ion gradient together with the aqueous phase in the internal region.

Now, each of the components will be described below.
Phospholipid

The phospholipid, which is one of main constituents of the lipid membrane in the liposome composition, is a main constituent of a biomembrane, and, in general, is an amphipathic substance which has both a hydrophobic group composed of a long chain alkyl group and a hydrophilic group composed of a phosphate group in its molecule. Examples of the phospholipid include: glycerophosphoric acids such as phosphatidylcholine (=lecithin), phosphatidylglycerol, phosphatidic acid, phosphatidylethanolamine, phosphatidylserine, phosphatidylinositol, etc.; sphingophospholipids such as sphingomyelin (SM), etc.; natural or synthetic diphosphatidyl phospholipids such as cardiolipin, etc. and their derivatives; hydrogenation products of these phospholipids such as hydrogenated soybean phosphatidylcholine (HSPC), hydrogenated egg yolk phosphatidylcholine, distearoylphosphatidylcholine, dipalmitoylphosphatidylcholine, and dimyristoylphosphatidylcholine. The phospholipids can be used either singly or in combination of a plurality of ones of them.

Additives Other Than Phospholipid

The membrane lipid in the liposome composition may include other membrane components together with the above-mentioned main constituent. For example, the liposome composition can contain other lipids than the phospholipids or derivatives of the other lipids, membrane stabilizers, antioxidants and the like, as required. The other lipids than the phospholipids are lipids having a hydrophobic group such as a long chain alkyl group in the molecule thereof but not containing a phosphate group in the molecule thereof, and are not specifically restricted. Examples of the other lipids include glyceroglycolipids, sphingoglycolipids, sterol derivatives such as cholesterol, and their derivatives such as their hydrogenation products. Examples of the cholesterol derivatives include those sterols which have a cyclopentanohydrophenanthrene ring. Among these, cholesterol is typically contained in the liposome composition. Examples of the antioxidants include ascorbic acid, uric acid, and tocopherol homologues, or vitamin E. Tocopherol includes four isomers, namely, $\alpha$-, $\beta$-, $\gamma$- and $\delta$-tocopherols, and any of them can be used.

The sum total of the phospholipid and cholesterol may be referred to also as total lipid.

The liposome composition can be made by selecting the following composition of the total lipid, which means the phospholipid and cholesterol.

1) The lipid membrane of the liposome is composed only of a phospholipid having an acyl chain of a saturated fatty acid with a chain length of 16 to 18.

2) Where the lipid membrane of the liposome includes a phospholipid having an acyl chain of a saturated fatty acid with a chain length of 14 to 18 and cholesterol as main constituents, the molar ratio of both the constituents is from 80:20 to 50:50.

3) Where the lipid membrane of the liposome includes a phospholipid having an acyl chain of an unsaturated fatty acid with a chain length of 16 to 18 and cholesterol as main constituents, the molar ratio of both the constituents is from 60:40 to 50:50.

As used herein, the chain length of the acyl chain means the number of carbon atoms in the acyl chain.

The saturated fatty acid with an acyl chain carbon atom number of 14 is myristic acid, the saturated fatty acid with an acyl chain carbon atom number of 15 is pentadecylic acid, the saturated fatty acid with an acyl chain carbon atom number of 16 is palmitic acid (trivial names: cetylic acid and hexadecylic acid, systematic name: hexadecanoic acid), the saturated fatty acid with an acyl chain carbon atom number of 17 is heptadecanoic acid, and saturated or unsaturated fatty acids with an acyl chain carbon atom number of 18 include stearic acid (systematic name: octadecanoic acid), oleic acid, linolic acid, and linolenic acid.

Internal Aqueous Phase (First Aqueous Phase) Solution of Liposome

For an internal aqueous phase solution of the liposome to be used for encapsulating an amphipathic weakly basic drug in the liposome at a high efficiency and stably, the selection of a counter ion to be encapsulated in the liposome together with the amphipathic weakly basic drug is a consideration. The liposome composition can contain sulfate ions, for encapsulating the drug at a high efficiency and achieving controlled-release properties lasting for a long time. While ammonium sulfate is generally used as a compound for generating sulfate ions, the compound for this purpose may also be selected from other compounds such as dekistran sulfate and chondroitin sulfate. In addition, other examples of the counter ion include inorganic or organic anions such as hydroxide, phosphate, glucuronate, citrate, carbonate, bicarbonate, nitrate, cyanate, acetate, benzoate, bromide, and chloride ions, as well as anionic polymers.

The pH of the internal aqueous phase differs according to the technique of the remote loading method. For example, in the case where citric acid is used, it is necessary to preliminarily form a pH gradient between the internal aqueous phase and the external aqueous phase. In this case, the pH difference between the internal aqueous phase and the external aqueous phase can be 3 or more. Besides, in the case where ammonium sulfate is used, a pH gradient is formed by chemical equilibrium, so that it is unnecessary to specially take the pH gradient into consideration.

In addition, in preparation of the liposome composition, the water-miscible organic solution containing the lipid in the water-miscible solvent is mixed with the first aqueous phase solution in an amount of 3/1 to 12/1 in terms of volume ratio to the water-miscible organic solution. The volume ratio of the first aqueous phase (internal aqueous phase) solution to the water-miscible organic solution can be in the range from 3 to 9, for example from 3 to 5.6.

External Aqueous Phase (Second Aqueous Phase) Solution of Liposome

As the external aqueous phase, there is used an aqueous solution which is lower than the internal aqueous phase solution in concentration of the ion for forming the above-mentioned ion gradient. Specific examples of the aqueous solution include an HEPES solution (hydroxyethyl piperazinesulfonic acid solution), a NaCl solution, and aqueous solutions of saccharides such as glucose and sucrose. The pH of the external aqueous phase is desirably controlled with a buffer. In consideration of decomposition of the lipid and the pH gap at the time of administration into a living body, the pH is preferably controlled to within the range from 5.5 to 8.5, for example the range of from 6.0 to 7.5. As for the osmotic pressures of the internal aqueous phase and the external aqueous phase of the liposome, they are not particularly limited insofar as they are controlled to within such ranges that the liposome will not be broken by the osmotic pressure difference between these aqueous phases. In consideration of physical stability of the liposome, a smaller osmotic pressure difference is more desirable.

Liposome Preparation

A drug can be encapsulated into the liposome composition by the remote loading method, whereby the liposome preparation is obtained.

Remote Loading Method

The remote loading method is a method for introducing a drug into liposomes by preparing empty liposomes without any drug encapsulated therein and adding the drug to an external liquid, namely, a liquid external to the liposomes. In the remote loading method, the drug added to the external liquid is actively transferred to the liposomes, to be taken into the liposomes. As a driving force for the active transfer, there is used a solubility gradient, an ion gradient, a pH gradient or the like. For example, a method is generally used in which a drug is introduced into the inside of liposomes by use of an ion gradient formed across the liposome membrane. As a specific example, there is a technology in which a drug is added to the inside of preliminarily formed liposomes by the remote loading method based on a Na+/K+ concentration gradient (see Japanese Patent No. 2847065).

In the remote loading method based on an ion gradient, a proton concentration gradient is most generally used. For example, a mode can be adopted in which a pH gradient such that the pH of the aqueous phase (internal aqueous phase) in the internal region of a liposome membrane is lower than the pH of the aqueous phase (external aqueous phase) in the external region of the liposome membrane is formed by use of citric acid. Besides, a pH gradient can be formed by an ammonium ion concentration gradient and/or a concentration gradient of an organic compound having an amino group which can be protonated (see Japanese Patent No. 2659136). In addition, in recent years, a method has been disclosed in which remote loading is carried out by introducing an ionophore into a liposome membrane (see U.S. Pat. Nos. 4,885,172, 5,059,421, 5,171,578, and 5,837,282).

Drug to be Encapsulated

The drug to be held in the liposome preparation is not specifically restricted insofar as the drug can be held inside the liposomes by the ion gradient method. For example, the drug can be an amphipathic weak base. In addition, from the viewpoint of effect, the drug can be a drug for which long-lasting controlled-release properties in local administration are desired. Particular examples of the drug are therapeutic agents for cerebral vascular disorder, Parkinson's disease, anti mental illness, dementia, etc. and analgesic agents. Examples of these drugs include donepezil, risperidone, rivastigmine, galanthamine, physostigmine, heptylphysostigmine, phenserine, tolserine, cymserine, thiatolserine, thiacymserine, neostigmine, Huperzine, tacrine, metrifonate, minocycline, fasudil hydrochloride, nimodine, morphine, bupivacaine, ropivacaine, levobupivacaine, tramadol, and lidocaine. Other examples include dopamine, L-DOPA, serotonin, epinephrine, codeine, meperidine, methadone, morphine, atropine, dicyclomine, metixene, propantheline, imipramine, amitriptyline, doxepin, desipramine, quinidine, propranolol, chlorpromazine, promethazine, and perphenazine.

Administering Method

The method for administering the liposome preparation is not specifically restricted. For example, the liposome preparation can be administered non-perorally and locally. For instance, subcutaneous, intramuscular, intraperitoneal, intrameningeal, extradural or intraventricular administration can be selected. The administering method can be appropriately selected according to the relevant symptom. A more particular administration method is subcutaneous or intramuscular. As a specific method for administration, the liposome preparation can be administered by use of a syringe or a spray-type device. In addition, local administration can be carried out through a catheter inserted in a living body, for example, in a body lumen, for instance, in a blood vessel, and led to a lesion part. The liposome preparation has systemic controlled-release properties such that the effective in-blood concentration of the drug encapsulated in the internal region of the liposome preparation can be maintained for at least four days. The liposome preparation has local controlled-release properties such that the effective local concentration of the drug encapsulated in the internal region of the liposome preparation can be maintained for at least four days. The liposome preparation has controlled-release properties such that the controlled-release properties of the drug continues for at least three days, for example at least four days, for example at least five days, and further for example at least seven days, after administration.

As used herein, the in-blood concentration means the concentration determined by sampling blood from a blood vessel and determining the concentration of the drug in the plasma by, for example, high performance liquid chromatography which will be described in Examples below.

The local concentration means the value obtained by sampling a specific part of a tissue, organ or the like and measuring the concentration of the drug in a supernatant obtained from a homogenate of the part. The effective concentration means the minimum concentration that is considered to be therapeutically effective and is determined according to the pathema and the kind of the drug.

A further illustrative embodiment provides a long-lasting controlled-release preparation kit that includes the above-mentioned liposome preparation and an injection needle of at least one gauge size selected from among 27 to 33 gauge. The number of the injection needles may be one or more than one, and the sizes of the injection needles may be either one or a combination of two or more. The liposome preparation of illustrative embodiments can be administered even by a thin needle such as a 27 gauge, 30 gauge or 33 gauge needle, so that the burden on the patient to be dosed with the drug is slight. In addition, the liposome preparation to be administered is high in controlled-release properties. Therefore, the long-lasting controlled-release preparation kit is high in usefulness.

EXAMPLES

Illustrative embodiments will be described in more detail below by showing Examples, but such illustrative embodiments are not restricted to the Examples. The concentration and particle diameter of each of drug-loaded liposomes prepared in Examples were determined as follows.

Phospholipid Concentration (mg/mL): Phospholipid concentration in a liposome suspension that is determined by high performance liquid chromatography or phospholipid determination.

Cholesterol Concentration (mg/mL): Cholesterol concentration in a liposome suspension that is determined by high performance liquid chromatography.

Total Lipid Concentration (mol/L): Total mol concentration (mM) of lipids as membrane constituents that is the sum total of the above-mentioned phospholipid concentration and cholesterol concentration.

Drug Concentrations (mg/mL)

(1) Concentration of Donepezil Hydrochloride (mg/mL): The liposome composition was diluted with RO water (reverse osmosis-purified water) so that the total lipid concentration of the preparation would be about 20 to 30 mg/mL. Then, the diluted liposome composition was further diluted with methanol by a factor of 20, and the liposome was disintegrated. For the resulting solution, absorbance at 315 nm was determined by high performance liquid chromatography using a UV-visible absorptiometer, to thereby obtain the concentration of donepezil hydrochloride in the preparation.

(2) Concentration of Bupivacaine Hydrochloride (mg/mL): The liposome composition was diluted with RO water (reverse osmosis-purified water) so that the total lipid concentration of the preparation would be about 20 to 30 mg/mL. Then, the diluted liposome composition was further diluted with methanol by a factor of 20, and the liposome was disintegrated. For the resulting solution, absorbance at 263 nm was determined by high performance liquid chromatography using a UV-visible absorptiometer, to thereby obtain the concentration of bupivacaine hydrochloride in the preparation.

(3) Concentration of Ropivacaine Hydrochloride (mg/mL): The liposome composition was diluted with RO water (reverse osmosis-purified water) so that the total lipid concentration of the preparation would be about 20 to 30 mg/mL. Then, the diluted liposome composition was further diluted with methanol by a factor of 20, and the liposome was disintegrated. For the resulting solution, absorbance at 263 nm was determined by high performance liquid chromatography using a UV-visible absorptiometer, to thereby obtain the concentration of ropivacaine hydrochloride in the preparation.

(4) Drug Support Amount (molar ratio of drug to total lipid): The molar ratio of the drug to the total lipid was obtained from the ratio of the concentration of the drug, namely, donepezil hydrochloride or bupivacaine hydrochloride or ropivacaine hydrochloride encapsulated in the liposomes to the above-mentioned total lipid concentration.

(5) Concentration of Donepezil Hydrochloride in Plasma (mg/mL): Sampled plasma was treated, and, for a supernatant obtained finally by centrifugation, fluorescence at an excitation wavelength (Ex) of 322 nm and a detection wavelength (Em) of 385 nm was determined by high performance liquid chromatography using a fluorophotometer, to thereby measure the concentration of donepezil hydrochloride in the plasma.

(6) Concentration of Bupivacaine Hydrochloride in Tissue (mg/mL): Sampled tissue was treated, and, for a supernatant obtained finally by centrifugation, absorbance at 210 nm was determined by high performance liquid chromatography using a UV-visible absorptiometer, to thereby measure the concentration of bupivacaine hydrochloride in the tissue.

(7) Average Particle Diameter (µm): Average particle diameter that is measured by a light scattering diffraction particle size distribution analyzer Beckman Coulter LS230.

The abridged names and molecular weights of the constituents used are set forth below.

HSPC: Hydrogenated soybean phosphatidylcholine (molecular weight 790, SPC3 produced by Lipoid GmbH)

Chol: Cholesterol (molecular weight 388.66, produced by Solvay S.A.)

DNP: Donepezil Hydrochloride (hereinafter sometimes referred to as DNP) (molecular weight 415.95, produced by UINAN CHENGHUI-SHUANFDA Chemical Co., Ltd.)

Bupivacaine Hydrochloride (molecular weight 324.89, produced by JINAN CHENGHUI-SHUANGDA Chemical Co., Ltd.)

Ropivacaine Hydrochloride (molecular weight 310.88, produced by JINAN CHENGHUI-SHUANGDA Chemical Co., Ltd.)

Comparison of Amounts of Drugs Encapsulated in Liposome Compositions Obtained in Different Control Conditions

Preparation Examples 1 to 3

Liposomes were prepared in a lipid concentration in ethanol of 150 w/v % or 200 w/v %, and a drug was introduced into the liposomes by a pH gradient, to prepare liposome preparations.

(1) Preparation of Empty Liposomes

HSPC and Chol were weighed in amounts as set forth in Table 1, and anhydrous ethanol was added thereto so that the concentration of lipids in anhydrous ethanol would be 150 w/v % or 200 w/v %, followed by dissolution with heating at about 70 degrees Celsius. Subsequently, the ethanol solution of the lipids obtained by the dissolution was admixed with an internal aqueous phase solution (150 mM aqueous ammonium sulfate solution) as the first aqueous phase in an amount of 4/1 or 3/1 (v/v) in terms of volume ratio to the ethanol solution of the lipids. The admixture was stirred with heating at a fixed rotating speed for 10 minutes, to thereby prepare empty liposomes. After the heating was over, the liposomes were immediately cooled with ice.

(2) Formation of pH Gradient

The ice-cooled empty liposomes were subjected to external liquid exchange by use of a centrifuge, to form a pH gradient between the internal aqueous phase side and the external aqueous phase side of the liposomes. The liposomes were then dispersed in about 10-fold amount of external aqueous phase (20 mM HEPES/0.9% sodium chloride (pH 7.5)), followed by centrifugation at 3,500 rpm for 15 minutes, to precipitate the liposomes. Thereafter, the supernatant was removed, and subsequently the liposomes were dispersed in 20 mM HEPES/0.9% sodium chloride of pH 7.5 added thereto, followed by centrifugation in the same manner as described above. This step was repeated three times, followed by re-dispersing in 20 mM HEPES/0.9% sodium chloride of pH 7.5, to form a pH gradient.

(3) Introduction of Drug by pH Gradient

After the formation of the pH gradient, the amounts of HSPC and cholesterol of the liposomes were determined, and total lipid concentration was calculated. Based on the total lipid concentration thus calculated, the amount of donepezil hydrochloride (DNP, molecular weight 415.95) for obtaining a DNP/total lipid (mol/mol) ratio of 0.16 was calculated. After the amount of DNP was weighed, a DNP solution (drug solution) in a concentration of 20 mg/mL was prepared by use of RO water.

A predetermined amount of the DNP solution preliminarily heated to 65 degrees Celsius was added to the liposome solution heated to 65 degrees Celsius, followed by heating and stirring at 65 degrees Celsius for 60 minutes, to effect introduction of the drug. After the introduction of the drug, the liposomes were immediately cooled with ice.

(4) Removal of Unencapsulated Drug

After the introduction of the drug, the liposomes were dispersed in the external aqueous phase solution (20 mM HEPES/0.9% sodium hydrochloride solution (pH 7.5)) added thereto, followed by centrifugation at 3,500 rpm for 15 minutes, to precipitate the liposomes. Thereafter, the supernatant was removed, and subsequently the liposomes were dispersed in 20 mM HEPES/0.9% sodium chloride solution (pH 7.5) added thereto, followed by centrifugation in the same manner as above. This step was repeated three times, thereby removing the unencapsulated drug.

For the liposome preparations of Preparation Examples 1 to 3 obtained by the producing method as above-mentioned, lipid concentration in ethanol, volume ratio of internal aqueous phase to lipid-containing ethanol solution, drug support amount (molar ratio of drug to total lipid), and particle diameter at the time of preparing empty liposomes are set forth in Table 2. It was made clear that a high drug support amount corresponding to a drug/(total lipid) molar ratio of equal to or more than 0.08 mol/mol can be obtained when the liposome preparation is prepared under the condition where the concentration of lipids in the ethanol solution and the volume ratio of the internal aqueous phase to the ethanol solution are as set forth in Table 2.

Figure 1:
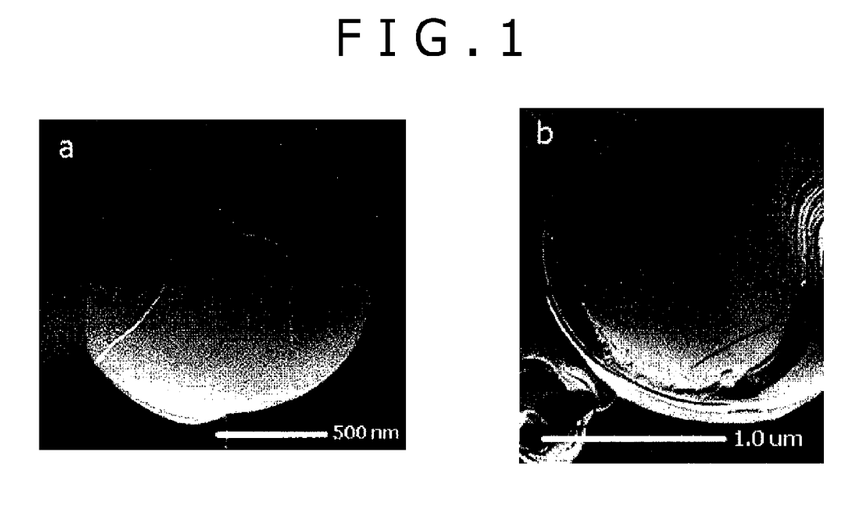
Figure 2:
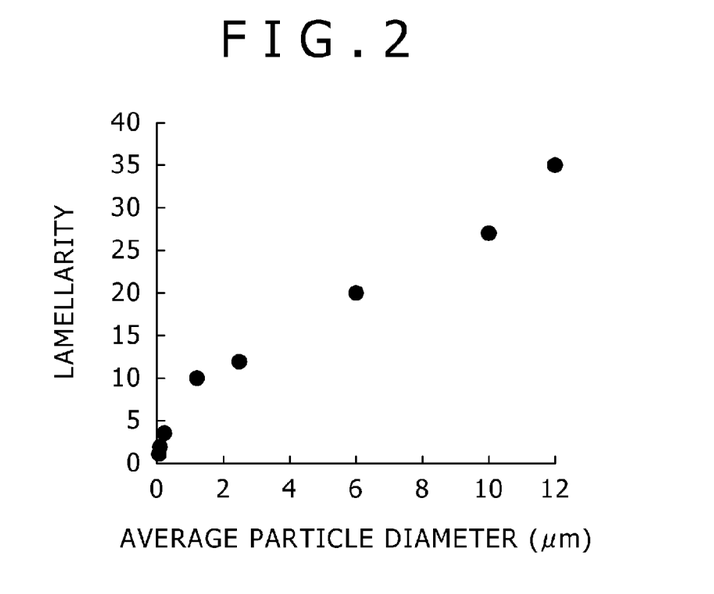
FIG. 2 is a graph showing the relationship between average particle diameter and the number of sheets of membranes (lamellarity).

FIG. 1 is a photograph upon transmission electron microscope (TEM) observation of a section of the liposome preparation after the drug introduction, produced in Preparation Example 2. The liposome preparation shown in FIG. 1a is fractured near the outermost surface of the liposome preparation. The liposome preparation shown in FIG. 1b is fractured substantially at the center of the liposome preparation. From the results of the electron microscope observation, it is seen that the liposome preparation is structured to have one homogenous internal aqueous phase, having an outer membrane composed of a plurality of lipid bilayers, as shown in FIG. 1. In addition, from the results of measurement of the number of lipid bilayers (layered structure, lamellarity) of the part showing high multiplicity (the part having a layered structure) when the electron microscope photograph is viewed by the naked eye, and when it is assumed that one set of lipid bilayer corresponds to one layered structure, the lamellarity of the liposome preparation with an average particle diameter of 6 μm obtained in an illustrative embodiment was about 20. Besides, the lamellarity of the liposome preparation with an average particle diameter of 2.5 μm was about 12. On the other hand, an average particle diameter for showing the long-lasting controlled-release properties of an illustrative preparation is equal to or greater than about 3 μm. Accordingly, while not wishing to be bound by any particular theory, it is considered that favorable controlled-release properties can be obtained when the lamellarity of the liposome preparation is equal to or more than 12 layers (preferably 12 to 27 layers).

Incidentally, the liposome preparation with an average particle diameter of 6 μm as measured in this Example is a liposome preparation wherein liposomes equal to or smaller than 3 μm are present in a proportion of less than about 10% (by volume or by number), liposomes equal to or greater than 10 μm are present in a proportion of about 10%, and liposomes measuring 4 to 7 μm are present in a proportion of equal to or more than about 50%.

TABLE 1

| | Total lipid | | | Internal aqueous phase |
|---|---|---|---|---|
| | HSPC | Chol | Ethanol | Ammonium sulfate |
| Preparation Example 1 | 2.12 g | 0.88 g | 2 mL | 8 mL |
| Preparation Example 2 | 2.82 g | 1.18 g | 2 mL | 8 mL |
| Preparation Example 3 | 2.81 g | 1.19 g | 2 mL | 6 mL |

Preparation Examples 4 and 5

DNP-loaded liposome preparations were prepared in the same manner as in Preparation Example 2, except that the rotating speed for the liposome suspension at the time of preparing empty liposomes was controlled to thereby control the particle diameter. The results are set forth in Table 2. As seen from the table, liposome preparations with different average particle diameters of 3.7 μm and 12.2 μm were obtained. In addition, liposome preparations with a high encapsulation efficiency and a large drug support amount were obtained, in the same manner as in Preparation Examples 1 to 3.

sition in Comparative Example 1 are set forth in Table 4. In addition, the drug support amount (molar ratio of drug to total lipid) and the particle diameter of the liposome com-

TABLE 2

|  | Total lipid concentration in ethanol (w/v %) | Volume ratio of IAP/ES* (v/v) | Kind of internal aqueous phase | Drug | Drug/ Total lipid (mol/mol) | Average particle diameter (μm) |
|---|---|---|---|---|---|---|
| Preparation Example 1 | 150 | 4/1 | 150 mM ammonium sulfate | Donepezil hydrochloride | 0.12 | 8.0 |
| Preparation Example 2 | 200 | 4/1 | 150 mM ammonium sulfate | Donepezil hydrochloride | 0.15 | 6.0 |
| Preparation Example 3 | 200 | 3/1 | 150 mM ammonium sulfate | Donepezil hydrochloride | 0.15 | 6.0 |
| Preparation Example 4 | 200 | 4/1 | 150 mM ammonium sulfate | Donepezil hydrochloride | 0.13 | 3.7 |
| Preparation Example 5 | 200 | 4/1 | 150 mM ammonium sulfate | Donepezil hydrochloride | 0.12 | 12.2 |
| Preparation Example 6 | 200 | 3/1 | pH 2.5 citric acid | Bupivacaine hydrochloride | 0.15 | 6.0 |
| Preparation Example 7 | 200 | 4/1 | pH 2.5 citric acid | Bupivacaine hydrochloride | 0.14 | 6.0 |
| Preparation Example 8 | 200 | 5.6/1 | pH 2.5 citric acid | Bupivacaine hydrochloride | 0.14 | 8.0 |
| Preparation Example 9 | 200 | 9/1 | pH 2.5 citric acid | Bupivacaine hydrochloride | 0.14 | 9.0 |
| Preparation Example 10 | 150 | 3/1 | pH 2.5 citric acid | Bupivacaine hydrochloride | 0.15 | 7.0 |
| Preparation Example 11 | 150 | 9/1 | pH 2.5 citric acid | Bupivacaine hydrochloride | 0.16 | 7.0 |
| Preparation Example 12 | 100 | 4/1 | pH 2.5 citric acid | Bupivacaine hydrochloride | 0.14 | 7.0 |
| Preparation Example 13 | 100 | 5.6/1 | pH 2.5 citric acid | Bupivacaine hydrochloride | 0.14 | 8.0 |
| Preparation Example 14 | 200 | 3/1 | 150 mM ammonium sulfate | Bupivacaine hydrochloride | 0.1 | 6.0 |
| Preparation Example 15 | 200 | 4/1 | 150 mM ammonium sulfate | Bupivacaine hydrochloride | 0.1 | 9.0 |
| Preparation Example 16 | 200 | 5.6/1 | 150 mM ammonium sulfate | Bupivacaine hydrochloride | 0.11 | 10 |
| Preparation Example 17 | 200 | 9/1 | 150 mM ammonium sulfate | Bupivacaine hydrochloride | 0.13 | 10 |
| Preparation Example 18 | 200 | 4/1 | 150 mM ammonium sulfate | Ropivacaine hydrochloride | 0.1 | 8.0 |

*IAP: internal aqueous phase, ES: ethanol solution

Comparative Example 1

Liposome Prepared when Lipid Concentration in Ethanol is 100 w/v %

HSPC and Chol were weighed in amounts set forth in Table 3, and 1 mL of anhydrous ethanol was added so that the lipid concentration in ethanol would be 100 w/v %, followed by dissolution with heating at about 70 degrees Celsius. Subsequently, the ethanol solution of lipids thus obtained was admixed with 9 mL of an internal aqueous phase solution (150 mM ammonium sulfate solution) as first aqueous phase so that the volume ratio to the ethanol solution would be 9/1, followed by heating and stirring at a fixed rotating speed for about 10 minutes, to prepare liposomes. The total lipid concentration in the mixed phase was 10 w/v %. After the heating was over, the empty liposomes were immediately cooled with ice. The subsequent formation of pH gradient, introduction of drug, and removal of unencapsulated drug were carried out by the same methods as in Preparation Examples 1 to 3, to obtain a drug-loaded liposome preparation.

The total lipid concentration in ethanol and the volume ratio of internal aqueous phase to ethanol solution at the time of preparing the empty liposomes of the liposome composition obtained are shown in Table 4. As a result, it was made clear that although an average particle diameter comparable to those in Preparation Examples 1 to 3 was obtained, the drug encapsulation amount is at a lowered level when the total lipid concentration in the mixed phase (internal aqueous phase solution+alcohol solution) is low (Table 4). From the foregoing, it is considered that the lipid concentration in ethanol and the volume ratio of internal aqueous phase to ethanol solution at the time of preparation of empty liposomes affect the liposome structure, consequently influencing the drug encapsulation amount.

TABLE 3

|  | Total lipid | | | Internal aqueous phase |
|---|---|---|---|---|
|  | HSPC | Chol | Ethanol | Ammonium sulfate |
| Comparative Example 1 | 0.71 g | 0.29 g | 1 mL | 9 mL |

TABLE 4

|  | Total lipid concentration in ethanol (w/v %) | Volume ratio of IAP/ES* (v/v) | Kind of internal aqueous phase | Drug | Drug/ Total lipid (mol/mol) | Average particle diameter (μm) |
|---|---|---|---|---|---|---|
| Comparative Example 1 | 100 | 9/1 | 150 mM ammonium sulfate | Donepezil hydrochloride | <0.08 | 8.0 |
| Comparative Example 2 |  |  | 150 mM ammonium sulfate | Donepezil hydrochloride | 0.13 | 0.3 |
| Comparative Example 3 |  |  | 150 mM ammonium sulfate | Donepezil hydrochloride | 0.15 | 1.2 |
| Comparative Example 4 | 200 | 2/1 | pH 2.5 citric acid | Bupivacaine hydrochloride | 0.13 | 9.0 |
| Comparative Example 5 | 150 | 2/1 | pH 2.5 citric acid | Bupivacaine hydrochloride | 0.12 | 8.0 |

TABLE 4-continued

|  | Total lipid concentration in ethanol (w/v %) | Volume ratio of IAP/ES* (v/v) | Kind of internal aqueous phase | Drug | Drug/ Total lipid (mol/mol) | Average particle diameter (μm) |
|---|---|---|---|---|---|---|
| Comparative Example 6 | 100 | 1.5/1 | pH 2.5 citric acid | Bupivacaine hydrochloride | 0.13 | 6.0 |
| Comparative Example 7 | 100 | 9/1 | pH 2.5 citric acid | Bupivacaine hydrochloride | 0.11 | 13 |

*IAP: internal aqueous phase, ES: ethanol solution

Preparation of Donepezil Hydrochloride Liposome Preparation by Extrusion Method

Comparative Examples 2 and 3

HSPC and Chol were weighed in respective amounts of 0.71 g and 0.29 g, and dissolved with heating in 1 mL of anhydrous ethanol added thereto. To 1 mL of the ethanol solution of lipids thus obtained, 9 mL of an ammonium sulfate solution (internal aqueous phase) heated to about 70 degrees Celsius was added, and the resulting admixture was stirred by an ultrasonic device with heating, to prepare a crude liposome suspension. The crude liposome suspension was sequentially passed through a filter (produced by Whatman plc) attached to an extruder (The Extruder T.10, produced by Lipexbiomembranes Inc.) heated to about 70 degrees Celsius; specifically, it was passed five times through a filter with a pore diameter of 0.4 μm or five times through a filter with a pore diameter of 2 μm, to prepare empty liposomes with a particle diameter of around 300 nm. After the heating was over, the empty liposomes were immediately cooled with ice. After the cooling with ice, external liquid exchange was conducted using gel filtration replaced sufficiently with an external aqueous phase (20 mM HEPES/0.9% sodium chloride solution (pH 7.5), to form a pH gradient. Thereafter, drug introduction was conducted by adding a predetermined amount of a DNP solution so that drug/total lipid (mol/mol)=0.16 and stirring with heating at 65 degrees Celsius for 60 minutes. After the drug introduction, the liposomes were immediately cooled with ice. Thereafter, removal of the unencapsulated drug was conducted by use of gel filtration replaced sufficiently with 20 mM HEPES/0.9% sodium chloride solution (pH 7.5).

Table 4 shows the drug support amounts and particle diameters of the liposome compositions prepared in Comparative Examples 2 and 3. As a result, liposome preparations with comparatively large drug support amounts were obtained.

Investigation of In Vitro Release Characteristics at Different Particle Diameters.

In this Example, drug release characteristics of the liposome compositions prepared in Preparation Examples 2, 4 and 5 and Comparative Examples 2 and 3 were examined by an in vitro evaluation system using ammonium sulfate.

Ammonium sulfate in an amount to attain a concentration of 7.5 mM was weighed, and a phosphate buffer was added thereto, to prepare a release test solution (7.5 mM ammonium sulfate/phosphate buffer, with pH 7.4 and 300 mOsmol). Each of the liposome compositions prepared in Preparation Examples 2, 4 and 5 and Comparative Examples 2 and 3 was diluted with the release test solution by a factor of 10, followed by heating at 37 degrees for a predetermined time. After 0, 1, 2, 5, 8, 10, 15, and 30 minutes from the start of the heating, a sample was taken out, a stop solution was immediately added to the sample, and the admixture was cooled with ice, to stop the release of drug. Determination of the amount of DNP released was carried out by high performance liquid chromatography according to the drug concentration determining method described above.

Figure 3:
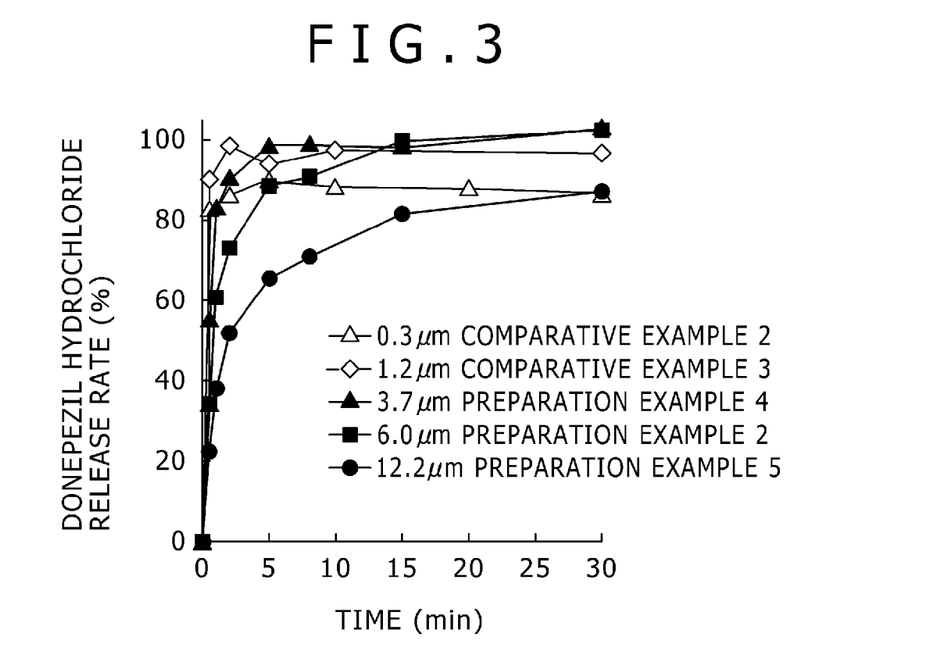
FIG. 3 is a graph showing release characteristics (the results of measurement by an in vitro release test method using ammonium sulfate) of release from liposome preparations having different particle diameters.
Figure 4:
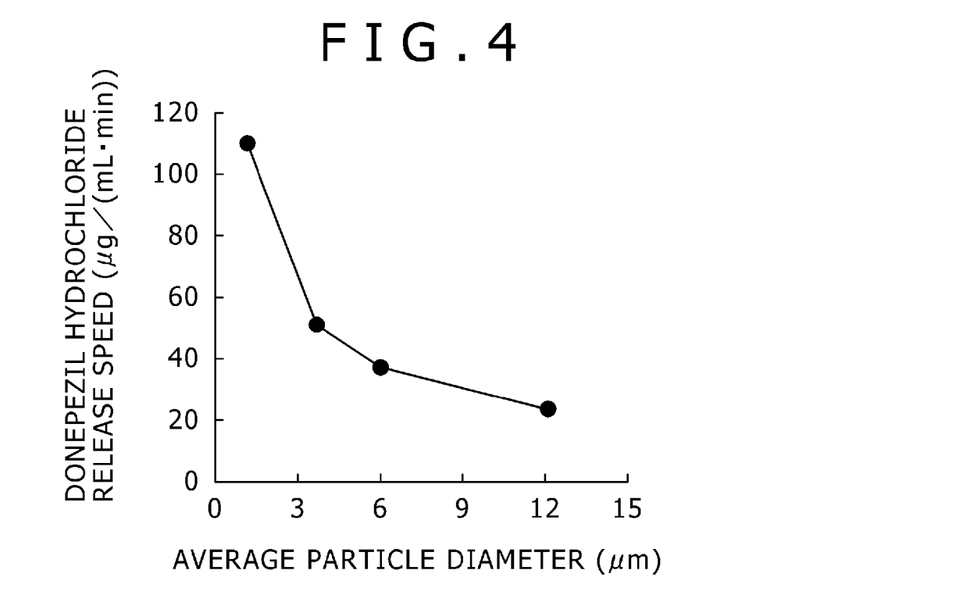
FIG. 4 is a graph showing the relationship between particle diameter and drug release speed.

As a result, it was clarified that the release of DNP (donepezil hydrochloride) from the liposomes is faster as the particle diameter is smaller, as shown in FIG. 3. Based on the data shown in FIG. 3, the inclinations of the plotted release curves in the beginning period were calculated, and the release speed at each average particle diameter was calculated. The results are shown in FIG. 4. The release speed was 23 (4/(mL·min)) at an average particle diameter of 12.2 μm, 37 (μg/(mL·min)) at an average particle diameter of 6 μm, 51 (μg/(mL·min)) at an average particle diameter of 3.7 μm, and 110 (μg/(mL·min)) at an average particle diameter of 1.2 μm.

From these results it was made clear that the release speed increases as the particle diameter decreases. Especially, when the average particle diameter was 1.2 μm, the release speed was conspicuously high. While not wishing to be bound by any particular theory, it is considered that when the average particle diameter is equal to or less than 1.2 μm, the drug is released in such a short time that continuousness cannot be obtained. While again not wishing to be bound by any particular theory, this is probably because the number of lipid membranes (the thickness of the layered structure) decreases as the particle diameter decreases, with the result that the drug diffuses to the outside of the liposomes more easily and the drug release is accelerated. Another one of the causes is considered to reside in that as the particle diameter is smaller, the curvature of the lipid membranes is greater, resulting in that the packing properties of the lipid membranes are weakened and the drug permeates through the lipid membranes more easily.

From these results it is clearly seen that the average particle diameter at which the release speed is conspicuously high and continuousness cannot be expected is 1.2 μm or below, and that an average particle diameter above 1.2 μm is important for realizing long-continuousness.

From the foregoing it is seen that the liposome compositions obtained in Comparative Examples 2 and 3 are high in drug encapsulation amount but are conspicuously high in release speed, as compared with the liposome compositions obtained in Preparation Examples 2, 4 and 5. Therefore, it can be difficult for the liposome compositions of Comparative Examples 2 and 3 to be released in vivo for a long period of at least three days. On the other hand, the liposome compositions of Preparation Examples 2, 4 and 5 show sustained-release profiles even in the in vitro release test; especially, it has become clear that the release speed is lower as the particle diameter is greater.

Pharmacokinetics of DNP Liposome

The donepezil liposome preparations produced in Preparation Example 2 and Comparative Examples 2 and 3 as well as donepezil used alone were subjected to a pharmacokinetic test. The liposome composition prepared by the described producing method can yield a high drug encapsulation amount and, therefore, enables administration of a drug in a small volume and in a high concentration. In view of this, the donepezil liposome preparation produced in Preparation Example 2 was subcutaneously administered into a back part of a rat in an amount of 50 mg/kg as an amount of donepezil hydrochloride. On the other hand, the liposome preparations produced in Comparative Examples 2 and 3 were limited in administerable volume in relation to the drug concentration in the preparation; in view of this, these liposome preparations were subcutaneously administered into a back part of a rat in respective amounts of 5 mg/kg and 25 mg/kg as an amount of donepezil hydrochloride. Furthermore, for comparison, donepezil used alone was subcutaneously administered into a back part of a rat in an amount of 5 mg/kg. The doses of donepezil hydrochloride used alone and the liposome preparations produced in Comparative Examples 2 and 3 and Preparation Example 2 are set forth in Table 5.

TABLE 5

| Preparation | Dose |
| --- | --- |
| Donepezil hydrochloride alone, subcutaneous administration (DNP alone) | SC 5 mg/kg |
| Comparative Example 2 | SC 5 mg/kg |
| Comparative Example 3 | SC 25 mg/kg |
| Comparative Example 2 | SC 50 mg/kg |

In the case of donepezil used alone, blood was sampled from a tail vein after 0.5, 1, 5, 10, 30, 120, 480, 1440, and 2880 minutes from the administration. For the liposome preparations, on the other hand, blood was sampled from a tail vein after 0.5, 1, 3, 4, 8, 24, 48, 72, 96, 120, 144, 168, 192, 216, 264, 288, 312, and 336 hours from the administration. The blood samples were each subjected to centrifugation (6,000 rpm, 10 minutes, 4 degrees), whereby plasma was obtained fractionally. The thus obtained plasma was treated, and the fluorescence intensity at an excitation wavelength (Ex) of 322 nm and a detection wavelength (Em) of 385 nm was determined by high performance liquid chromatography, thereby determining the concentration of donepezil hydrochloride in each plasma sample. The results are shown in FIG. 5.

Figure 5:
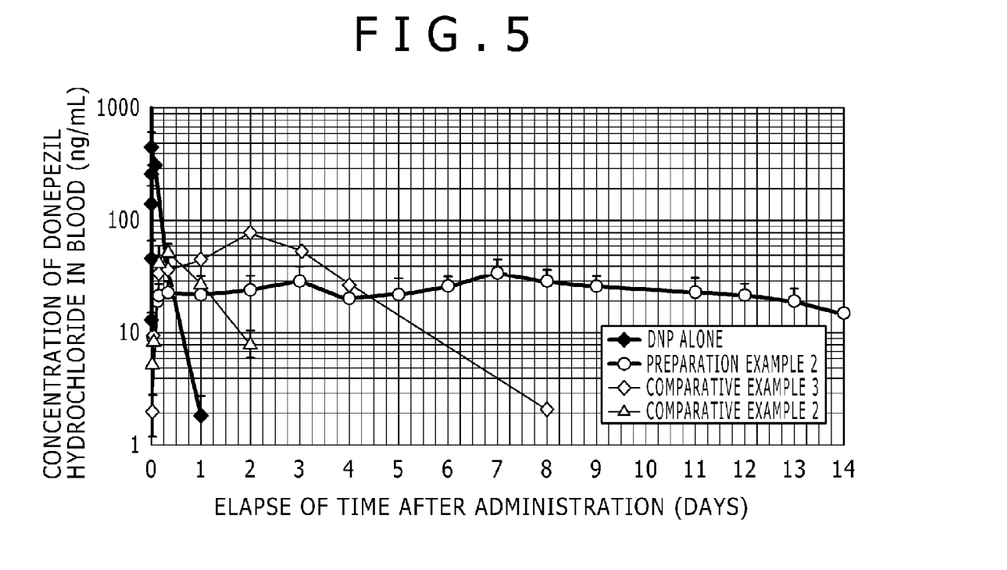
FIG. 5 is a graph showing the concentration of donepezil hydrochloride in blood after subcutaneous administration of donepezil alone and liposome preparations.

As shown in FIG. 5, the concentration of donepezil hydrochloride in blood in the case of subcutaneous administration of donepezil hydrochloride alone showed a maximum in-blood concentration after 0.5 hour from the administration, and then decreased rapidly. After 48 hours, the concentration had already been lowered below the detection limit. The liposome preparation prepared in Comparative Example 2 did not show an initial burst, as contrasted to donepezil used alone. Besides, although this preparation showed long-lasting controlled-release until 48 hours passed, its concentration in blood reached a maximum after eight hours from the administration, was then lowered rapidly, and already lowered below 10 ng/ml after 48 hours from the administration. The liposome preparation prepared in Comparative Example 3 maintained a comparatively high drug concentration in blood for four days after the administration, but thereafter the concentration was lowered rapidly. These preparations have comparatively small particle diameters of 0.3 μm and 1.2 μm, respectively, so that the release characteristics of drug from these liposome preparations is faster than the release characteristics from liposome preparations with larger particle diameters. In addition, it may be considered in these cases that the liposomes are liable to diffuse in the administration region, and transferred into lympha or blood, so that the liposomes are lost speedily. For these reasons, it is supposed that the expected long-lasting controlled-release properties cannot be obtained.

On the other hand, the liposome preparation obtained in Preparation Example 2 did not show the initial burst, and showed a marked prolongation of controlled-release time; thus, controlled-release properties lasting for a long period of four days could be obtained. The reason is considered as follows. The presence of the pH gradient permits the drug to be firmly held in the internal aqueous phase. In addition, as the particle diameter increases, the number of the lipid bilayers increases, and the layered structure becomes thicker, so that permeability of the drug through the lipid membrane is suppressed. As a result, the controlled-release properties lasting for a long period of time could be attained.

The drug concentration in blood obtained in this Example shows an effective concentration which is sufficient on a clinical basis. The absence of the initial burst and the ability to stably maintain an effective concentration for four days ensure that the fear of side effects is eliminated and that the quality of life of the patient can be enhanced. Consequently, a preparation having a very effective controlled-release ability could be obtained.

From the foregoing, it is understood that the liposome composition prepared according to an illustrative embodiment has one internal aqueous phase with an outer membrane composed of a plurality of lipid bilayers, and permits a sufficient amount of a drug to be firmly held in the internal aqueous phase by the pH gradient method, thereby enabling the drug to be encapsulated in a high concentration. Besides, the liposome preparation of an illustrative embodiment wherein a drug is encapsulated in the liposome composition is an excellent long-lasting controlled-release preparation which exhibits controlled-release properties lasting for a long period of time.

Preparation of Bupivacaine Hydrochloride Liposome Preparation According to an Illustrative Embodiment Comparative Examples 6 to 13

HSPC and Chol were weighed in respective amounts as set forth in Table 6, and anhydrous ethanol was added thereto so that the lipid concentration in anhydrous ethanol would be 200, 150 and 100 w/v %, respectively, followed by dissolution with heating at about 70 degrees Celsius. Subsequently, the ethanol solutions of lipids thus obtained were each admixed with an internal aqueous phase solution (citric acid solution of pH 2.5) in respective amounts of 3/1, 4/1, 5.6/1, and 9/1 (v/v) in terms of volume ratio to the ethanol solution, and the resulting admixtures were each stirred with heating at a fixed rotating speed for about 10 minutes, to prepare liposomes. After the heating was over, the liposomes were immediately cooled with ice. The relationships of ethanol, internal aqueous phase, and lipid concentration in the preparation conditions are set forth in Table 7.

Thereafter, external liquid exchange was conducted by a centrifuge using a citric acid solution of pH 6.5, thereby forming a pH gradient between the inside and the outside of the liposomes.

Subsequently, drug introduction was conducted in the same manner as in Preparation Examples 1 to 3. As the drug, bupivacaine hydrochloride (BPV, molecular weight 324.89) was used. After a required amount of bupivacaine hydrochloride (BPV) was weighed, RO water was added thereto to prepare a 10 mg/mL BPV solution (drug solution), and drug introduction was conducted by stirring with heating at 65 degrees Celsius for 60 minutes. After the drug introduction, the liposomes were immediately cooled with ice. Subsequently, using a citric acid solution of pH 6.5, removal of unencapsulated drug was conducted by the same procedure as in Preparation Examples 1 to 3. For the bupivacaine hydrochloride liposomes thus obtained, the molar ratio (mol/mol) of bupivacaine hydrochloride to total lipid is shown in Table 8 as drug encapsulation amount.

Consequently, very high values of drug encapsulation amount as shown in Table 8 were obtained when the lipid concentration in ethanol was 100 to 200 w/v %, the internal aqueous phase (citric acid solution of pH 2.5) was added in amounts of 3/1, 4/1, 5.6/1, and 9/1 (v/v) in terms of volume ratio to the ethanol solution, and the lipid concentration was 15 to 50 w/v % based on the total volume of the ethanol solution and the internal aqueous phase (mixed phase) as shown in Tables 2 and 7.

TABLE 6

| | Lipids | | Volume of ethanol | Internal aqueous phase solution (pH 2.5 citric acid solution) |
|---|---|---|---|---|
| | HSPC | Chol | | |
| Preparation Example 6 | 2.8 g | 1.2 g | 2 mL | 6 mL |
| Preparation Example 7 | 2.8 g | 1.2 g | 2 mL | 8 mL |
| Preparation Example 8 | 2.8 g | 1.2 g | 2 mL | 11.2 mL |
| Preparation Example 9 | 2.8 g | 1.2 g | 2 mL | 18 mL |
| Preparation Example 10 | 2.8 g | 1.2 g | 2.6 mL | 7.8 mL |
| Preparation Example 11 | 2.8 g | 1.2 g | 2.6 mL | 23.4 mL |
| Preparation Example 12 | 2.8 g | 1.2 g | 4 mL | 16 mL |
| Preparation Example 13 | 2.8 g | 1.2 g | 4 mL | 22.4 mL |

Here, numerical values in Prep. Ex. (Preparation Example) and Comp.Ex. (Comparative Example) indicate the molar ratio (mol/mol) of bupivacaine hydrochloride to total lipid.

Preparation Examples 14 to 17

Bupivacaine hydrochloride liposomes were prepared in the same manner as in Preparation Examples 6 to 9, except that a 150 mM ammonium sulfate was used as the internal aqueous phase. HSPC and Chol were weighed in respective amounts as set forth in Table 9, and anhydrous ethanol was added thereto so that the lipid concentration in anhydrous ethanol would be 200 w/v %, followed by dissolution with heating at about 70 degrees Celsius. Subsequently, using a 150 mM ammonium sulfate as the internal aqueous phase, the internal aqueous phase solution (150 mM ammonium sulfate) was added to the above-obtained ethanol solution of lipids in respective amounts of 3/1, 4/1, 5.6/1, and 9/1 (v/v) in terms of volume ratio to the ethanol solution, followed by stirring with heating at a fixed rotating speed for about 10 minutes, to prepare empty liposomes. After the heating was over, the liposomes were immediately cooled with ice.

Thereafter, formation of pH gradient, introduction of bupivacaine hydrochloride, and removal of unencapsulated drug were carried out in the same manner as in Preparation Examples 6 to 9, to obtain bupivacaine hydrochloride liposome preparations. The results are set forth in Table 2. In the case where ammonium sulfate was used as the internal aqueous phase, also, high values of drug encapsulation amount were obtained in the same manner as in the case where the citric acid solution of pH 2.5 was used.

TABLE 7

| | | Internal aqueous phase/Ethanol soln. of lipid [volume ratio] | | | | | | |
|---|---|---|---|---|---|---|---|---|
| | | 1/1 | 1.5/1 | 2/1 | 3/1 | 4/1 | 5.6/1 | 9/1 |
| Lipid concentration in ethanol | 200 w/v % | | | (LP 67%) | (LP 50%) | (LP 40%) | (LP 30%) | (LP 20%) |
| | 150 w/v % | | | (LP 51%) | (LP 38%) | (LP 30%) | (LP 23%) | (LP 15%) |
| | 100 w/v % | (LP 50%) | (LP 40%) | (LP 33%) | (LP 25%) | (LP 20%) | (LP 15%) | (LP 10%) |

Here, LP (lipid concentration) % indicates the total lipid (w/v %) in the mixed phase.

Here, LP (lipid concentration) % indicates the total lipid (w/v %) in the mixed phase.

TABLE 8

| | | Internal aqueous phase/Ethanol Soln. of lipid [volume ratio] | | | | | | |
|---|---|---|---|---|---|---|---|---|
| | | 1/1 | 1.5/1 | 2/1 | 3/1 | 4/1 | 5.6/1 | 9/1 |
| Lipid concentration in ethanol | 200 w/v % | | | Comp. Ex. 4 0.13 | Prep. Ex. 6 0.15 | Prep. Ex. 7 0.14 | Prep. Ex. 8 0.14 | Prep. Ex. 9 0.14 |
| | 150 w/v % | | | Comp. Ex. 5 0.12 | Prep. Ex. 10 0.15 | | | Prep. Ex. 11 0.16 |
| | 100 w/v % | | Comp. Ex. 6 0.13 | | | Prep. Ex. 12 0.14 | Prep. Ex. 13 0.14 | Comp. Ex. 7 0.11 |

Here, numerical values in Prep. Ex. (Preparation Example) and Comp. Ex. (Comparative Example) indicate the molar ratio (mol/mol) of bupivacaine hydrochloride to total lipid.

TABLE 9

|  | Total lipid | | | Internal aqueous phase 150 mM |
|---|---|---|---|---|
|  | HSPC | Chol | Ethanol | ammonium sulfate |
| Preparation Example 14 | 2.8 g | 1.2 g | 2 mL | 6 mL |
| Preparation Example 15 | 2.8 g | 1.2 g | 2 mL | 8 mL |
| Preparation Example 16 | 2.8 g | 1.2 g | 2 mL | 11.2 mL |
| Preparation Example 17 | 2.8 g | 1.2 g | 2 mL | 18 mL |

Comparative Examples 4 to 7

HSPC and Chol were weighed in amounts set forth in Table 10, and anhydrous ethanol was added thereto so that the lipid concentration in anhydrous ethanol would be 200, 150 and 100 w/v %, respectively, followed by dissolution with heating at about 70 degrees Celsius. Subsequently, an internal aqueous phase (citric acid solution of pH 2.5) was added to the above-obtained ethanol solutions of lipids in respective amounts of 1.5/1, 2/1, and 9/1 (v/v) in terms of volume ratio to the ethanol solution, followed by stirring with heating at a fixed rotating speed for about 10 minutes, to prepare liposomes. After the heating was over, the liposomes were immediately cooled with ice.

Thereafter, external liquid exchange was conducted using a citric acid solution of pH 6.5, to form a pH gradient between the internal aqueous phase and the external aqueous phase of the liposomes. Subsequently, drug introduction was conducted using bupivacaine hydrochloride.

Subsequently, removal of unencapsulated drug was conducted using a citric acid solution of pH 6.5, to obtain liposome preparations. For the thus obtained liposome preparations, bupivacaine hydrochloride encapsulation amounts are shown in Tables 4 and 8.

As a result, it was found that when the lipid concentration in ethanol was 100 to 200 w/v % and the volume ratio of the internal aqueous phase (citric acid solution of pH 2.5) to the ethanol solution of lipids was equal to or less than 2/1, the drug encapsulation amount was somewhat decreased and the amount of unencapsulated drug (the ratio of the amount of bupivacaine hydrochloride in the external liquid to the amount of bupivacaine hydrochloride in preparation) was comparatively high as 6 to 9%. The foregoing suggests that under the above-mentioned liposome preparation conditions, a sufficient amount of drug cannot be stably held in the internal aqueous phase.

TABLE 10

|  | Lipids | | | Internal aqueous phase solution (pH 2.5 citric acid solution) |
|---|---|---|---|---|
|  | HSPC | Chol | Ethanol |  |
| Comparative Example 4 | 2.8 g | 1.2 g | 2 mL | 4 mL |
| Comparative Example 5 | 2.8 g | 1.2 g | 2.6 mL | 5.2 mL |
| Comparative Example 6 | 2.8 g | 1.2 g | 4 mL | 6 mL |
| Comparative Example 7 | 2.8 g | 1.2 g | 4 mL | 36 mL |

Pharmacokinetics of Bupivacaine Hydrochloride Liposome Preparation

Figure 6:
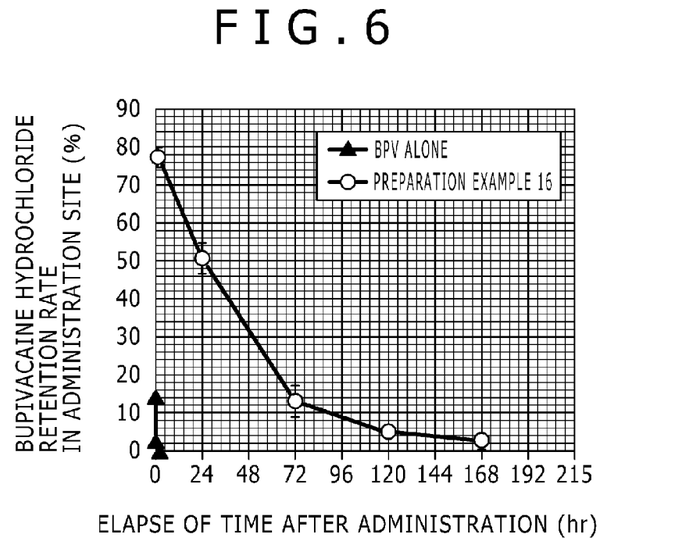
FIG. 6 is a graph showing bupivacaine hydrochloride retention rate (mass %) in an administration site after intramuscular administration of bupivacaine hydrochloride alone and a liposome preparation.

The bupivacaine hydrochloride liposome preparation prepared in Preparation Example 16 and bupivacaine hydrochloride used alone were subjected to a pharmacokinetic test. The liposome preparation and bupivacaine hydrochloride used alone were administered subcutaneously into a back part of a rat in respective doses as set forth in Table 11 while the doses are set as the amount of bupivacaine hydrochloride. After the lapse of 1, 24, 72, 120, and 168 hours from the administration of the bupivacaine hydrochloride liposome composition, and after the lapse of 0.5, 4, and 24 hours from the administration of bupivacaine hydrochloride used alone, a subcutaneous tissue of the back part in the administration site was sampled and subjected to a homogenizing treatment. Subsequently, the homogenate solution was treated, and the sample solution thus obtained was subjected to determination by high performance liquid chromatography, to determine the amount of bupivacaine hydrochloride remaining in the subcutaneous tissue of the back part in the administration site. The results are shown in FIG. 6. The retention rate of bupivacaine hydrochloride used alone in the administration site was lowered to below 1% in four hours after the administration. From this result, it was verified that bupivacaine hydrochloride used alone disappears from the administration site in several hours. On the other hand, the bupivacaine hydrochloride liposome preparation gave a profile of sustained losing from the administration site depending on the lapse of time. In this case, bupivacaine hydrochloride remained in the administration site in an amount of about 10% on the third day, about 5% on the fifth day, and about 3% on the seventh day from the administration. From these results, it was clear that the liposomes released bupivacaine hydrochloride at the administration site in a sustained manner.

From the foregoing, the bupivacaine hydrochloride liposome preparation obtained according to illustrative embodiments have a long-lasting controlled-release ability.

TABLE 11

| Preparation | Dose |
|---|---|
| Bupivacaine hydrochloride alone, subcutaneous administration | SC 3.5 mg/kg |
| Preparation Example 16 | SC 3.5 mg/kg |

Preparation of Ropivacaine Hydrochloride Liposome According to and Illustrative Embodiment Preparation Example 18

A liposome composition was produced in the same manner as in Preparation Example 15, except for using ropivacaine hydrochloride as the drug, to obtain ropivacaine hydrochloride liposomes.

Consequently, as shown in Table 1, in the case where ropivacaine hydrochloride was used as the drug, the drug can be introduced by the pH gradient method, and a high value of drug encapsulation amount was obtained. Besides, in regard of in vitro release properties, a release profile similar to those of the donepezil hydrochloride liposome preparation and the bupivacaine hydrochloride liposome preparation was obtained.

Confirmation of Size of Injection Needle for Administration of Liposome Preparation of Illustrative Embodiments Down to what level of needle thinness the administration of the liposome preparation of an illustrative embodiment can be carried out was investigated. Using the liposome preparation containing bupivacaine hydrochloride which was prepared in Preparation Example 16, a step of drawing in the preparation and a step of pushing out the preparation into and from injection needles of different gauges were performed. As a result, the liposome preparation of illustrative embodiments could be easily drawn in and pushed out by any of the very thin injection needles, as thin as 27 gauge, 30 gauge, and 33 gauge.

Comparative Experiment

As a comparative experiment in relation to the above, the determination of whether Risperdal Consta (produced by Janssen Pharmaceutical K.K.) can be administered by thin injection needles was investigated. Risperdal Consta is a name for microspheres composed of polylactic acid-glycolic acid copolymer (PLGA). Specifically, it is a continuous injection of an antipsychotic, in the form of a kit product provided with a 200 injection needle. The microspheres have an average particle diameter of 25 to 150 µm. An operation of drawing these microspheres was tried using 27 to 33 gauge injection needles. As a result, none of the 27 to 33 gauge injection needles could be successfully used to draw the microspheres. As for a step of pushing out the microspheres, only thick injection needles of 19 to 21 gauge could be used for administration, while thin injection needles of 27 gauge, 30 gauge and 33 gauge could not be successfully used to push out the microspheres. It is considered that the particle size of the microspheres is so large that the microspheres cannot be administered using thin needles.

From the foregoing, it has been found that the thinner limit of needle gauge for administration of microspheres such as liposomes has ordinarily been at around 19 to 21 gauge, but that the liposome preparation according to the illustrative embodiments can be administered using such thin needles as 27 gauge, 30 gauge and 33 gauge needles.

The detailed description above describes a long-lasting controlled-release liposome composition disclosed by way of example. The invention is not limited, however, to the precise embodiment and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method of preparing a liposome composition comprising mixing a water-miscible organic solution, in which a phospholipid and cholesterol are contained in a total concentration of 100 to 200 w/v % in the water-miscible organic solvent, with a first aqueous phase solution in an amount of 3/1 to 12/1 in terms of volume ratio to the water-miscible organic solution, thereby obtaining an emulsion in which the total concentration of the phospholipid and cholesterol in the resulting mixed phase is 15 to 50 w/v %; and subjecting the emulsion to external solution exchange with a second aqueous phase solution thereby forming an ion gradient between an aqueous phase in an internal region of a liposome membrane, the internal-region aqueous phase including the first aqueous phase solution, and an aqueous phase in an external region of the liposome membrane, the external-region aqueous phase including the second aqueous phase solution, wherein the internal-region aqueous phase is inside a multilayer membrane having a layered structure of at least 12 concentric layers.

2. The method according to claim 1, wherein the ion gradient is the pH proton gradient, and the liposome composition has a pH gradient such that the pH of the aqueous phase in the internal region of a liposome is lower than the pH of the aqueous phase in the external region of the liposome.

3. The method according to claim 1, wherein the liposome has the internal-region aqueous phase inside a multilayer membrane having an average particle diameter in terms of outermost diameter of equal to or greater than 2.5 µm.

4. A method of preparing a liposome preparation comprising introducing a drug into the aqueous phase in the internal region in the liposome composition prepared according to claim 1 by an ion gradient, wherein the drug is held in the liposome in a molar ratio of equal to or more than 0.08 based on the total lipid.

5. The method of preparing a liposome preparation according to claim 4, wherein the liposome preparation has either systemic controlled-release properties, such that an in-blood effective concentration of the drug encapsulated in the internal region is maintained for equal to or more than four days, or local controlled-release properties, such that a local effective concentration of the drug encapsulated in the internal region is maintained for equal to or more than four days.

6. The method of preparing a liposome preparation according to claim 4, wherein the drug is an amphipathic weakly basic compound.

7. The method according to claim 2, wherein the liposome has the internal-region aqueous phase inside a multilayer membrane having an average particle diameter in terms of outermost diameter of equal to or greater than 2.5 µm.

8. A method of preparing a liposome preparation comprising introducing a drug introduced into the aqueous phase in the internal region in the liposome composition prepared according to claim 7 by an ion gradient, wherein the drug is held in the liposome in a molar ratio of equal to or more than 0.08 based on the total lipid.

9. The method of preparing a liposome preparation according to claim 8, wherein the liposome preparation has either systemic controlled-release properties, such that an in-blood effective concentration of the drug encapsulated in the internal region is maintained for equal to or more than four days, or local controlled-release properties, such that a local effective concentration of the drug encapsulated in the internal region is maintained for equal to or more than four days.

10. The method of preparing a liposome preparation according to claim 9, wherein the drug is an amphipathic weakly basic compound.

11. The method according to claim 1, wherein the phospholipid is a hydrogenated soybean phosphatidylcholine.

12. The method according to claim 1, wherein the liposome has a layered structure of 12 to 35 layers.

13. The method according to claim 1, wherein the liposome has an average particle diameter of 2.5 to 12 µm.

14. The method of preparing a liposome preparation according to claim 4, wherein the drug is selected from the group consisting of bupivacaine hydrochloride, ropivacaine hydrochloride, and donepezil hydrochloride.

15. The method of preparing a liposome composition according to claim 4, wherein the drug is donepezil hydrochloride.

16. The method according to claim 1, wherein the liposome of the liposome composition is not a multivesicular liposome.

17. The method according to claim 1, wherein the first aqueous phase solution is in an amount of 3/1 to 9/1 in terms of volume ratio to the water-miscible organic solution.

18. A method of preparing a liposome preparation, comprising a liposome composition and a drug, said method comprising:

mixing a water-miscible organic solution, in which a phospholipid and cholesterol are contained in a total concentration of 100 to 200 w/v % in a water-miscible organic solvent, with a first aqueous phase solution in an amount of 3/1 to 12/1 in terms of volume ratio to the water-miscible organic solution, thereby obtaining an emulsion in which the total concentration of the phospholipid and cholesterol in the resulting mixed phase is 15 to 50 w/v %, followed by subjecting the emulsion to external solution exchange with a second aqueous phase solution, wherein an ion gradient is formed between an aqueous phase in an internal region of a liposome membrane, the internal-region aqueous phase including the first aqueous phase solution, and an aqueous phase in an external region of the liposome membrane, the external-region aqueous phase including the second aqueous phase solution, wherein the internal-region aqueous phase is inside a multilayer membrane having a layered structure of at least 12 concentric layers to thereby provide the liposome composition, and introducing the drug into the aqueous phase in the internal region in the liposome composition by an ion gradient, wherein the drug is held in the liposome in a molar ratio of from 0.08 to 0.16 based on the total lipid.

* * * * *